United States Patent [19]

Pennington, Sr. et al.

[11] 4,241,601
[45] Dec. 30, 1980

[54] PRE-SET AUTOMATICALLY OPERABLE MEANS FOR MEASURING THE PLASTICITY OF TEST SPECIMENS INCLUDING APPARATUS FOR INDICATING AND RECORDING THE RESULTS THEREOF

[75] Inventors: Fred A. Pennington, Sr., Naples, Fla.; Fred A. Pennington, Jr., Shiremanstown; John W. Porr, Jr., New Cumberland, both of Pa.

[73] Assignee: Andrew S. McCreath & Son, Inc., Harrisburg, Pa.

[21] Appl. No.: 14,571

[22] Filed: Feb. 23, 1979

[51] Int. Cl.³ ............................................ G01N 25/04
[52] U.S. Cl. ....................................... 73/17 R; 73/59
[58] Field of Search ................................. 73/17 R, 59

[56] References Cited
U.S. PATENT DOCUMENTS
4,074,561  2/1978  Brockschmidt et al. ............ 73/17 R

*Primary Examiner*—Gerald Goldberg
*Assistant Examiner*—Joseph W. Roskos

[57] ABSTRACT

A pre-set and automatically operable means measures the plasticity of heated coal specimens or other material to be tested, and certain results thereof are indicated on visual read-out devices while other results are recorded in print-indicating instrumentalities, including signalling devices, are provided to keep the operator of the apparatus informed as to progress being made. A prime feature is the inclusion of several separate and closely adjacent specimen containers with the test specimen therein in heated condition, one of which may be in testing position while the other is in standby position with heated specimen intact and awaiting its turn to be moved into operating position. Means are provided for so supporting those portions of the testing apparatus which extend into or are connected with the specimen container with the specimen being tested, that they may be easily and quickly elevated at the conclusion of the test and just as easily and rapidly restored to such positions with respect to the appropriately heated specimen and its container which are in a standby position.

10 Claims, 6 Drawing Figures

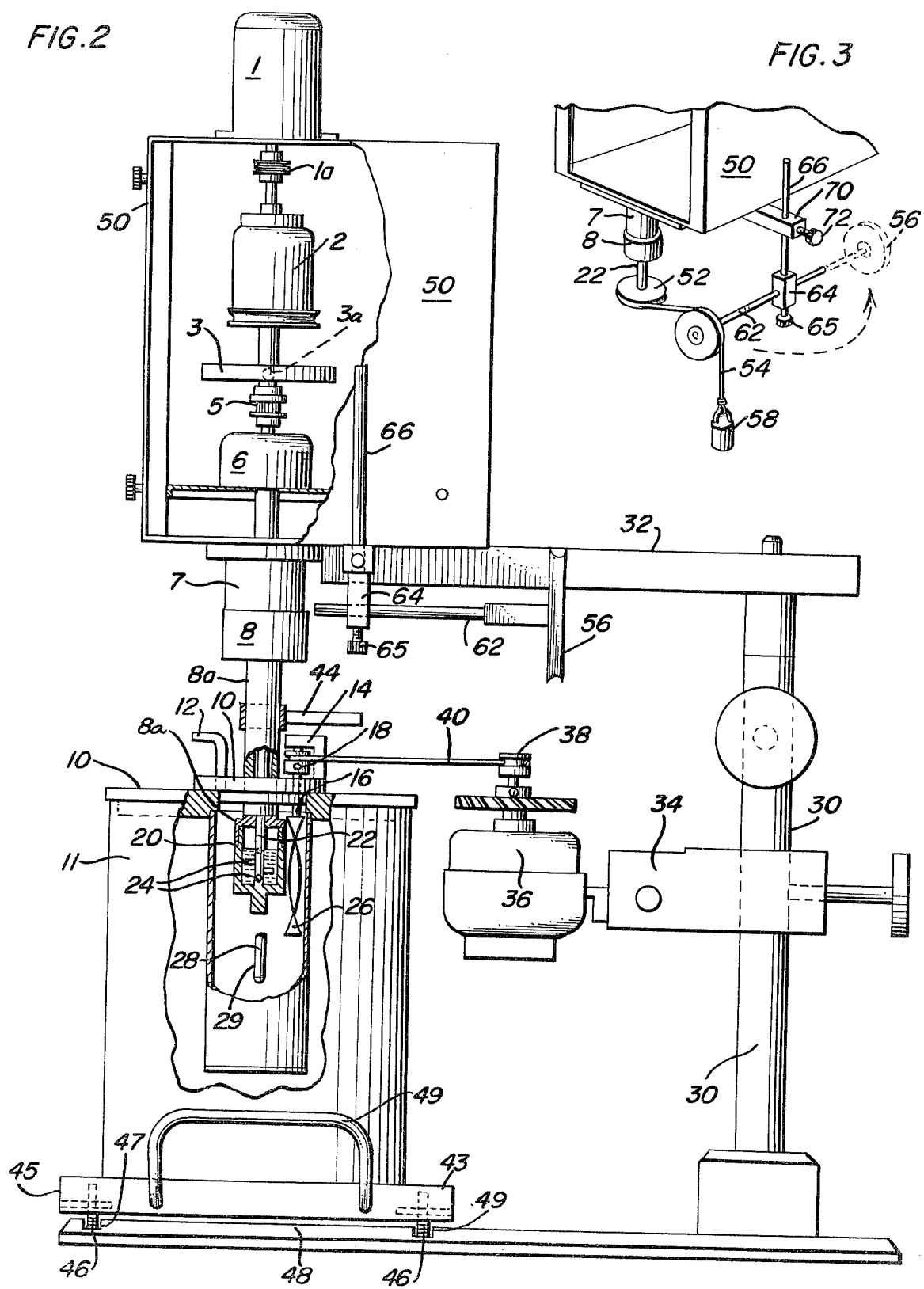

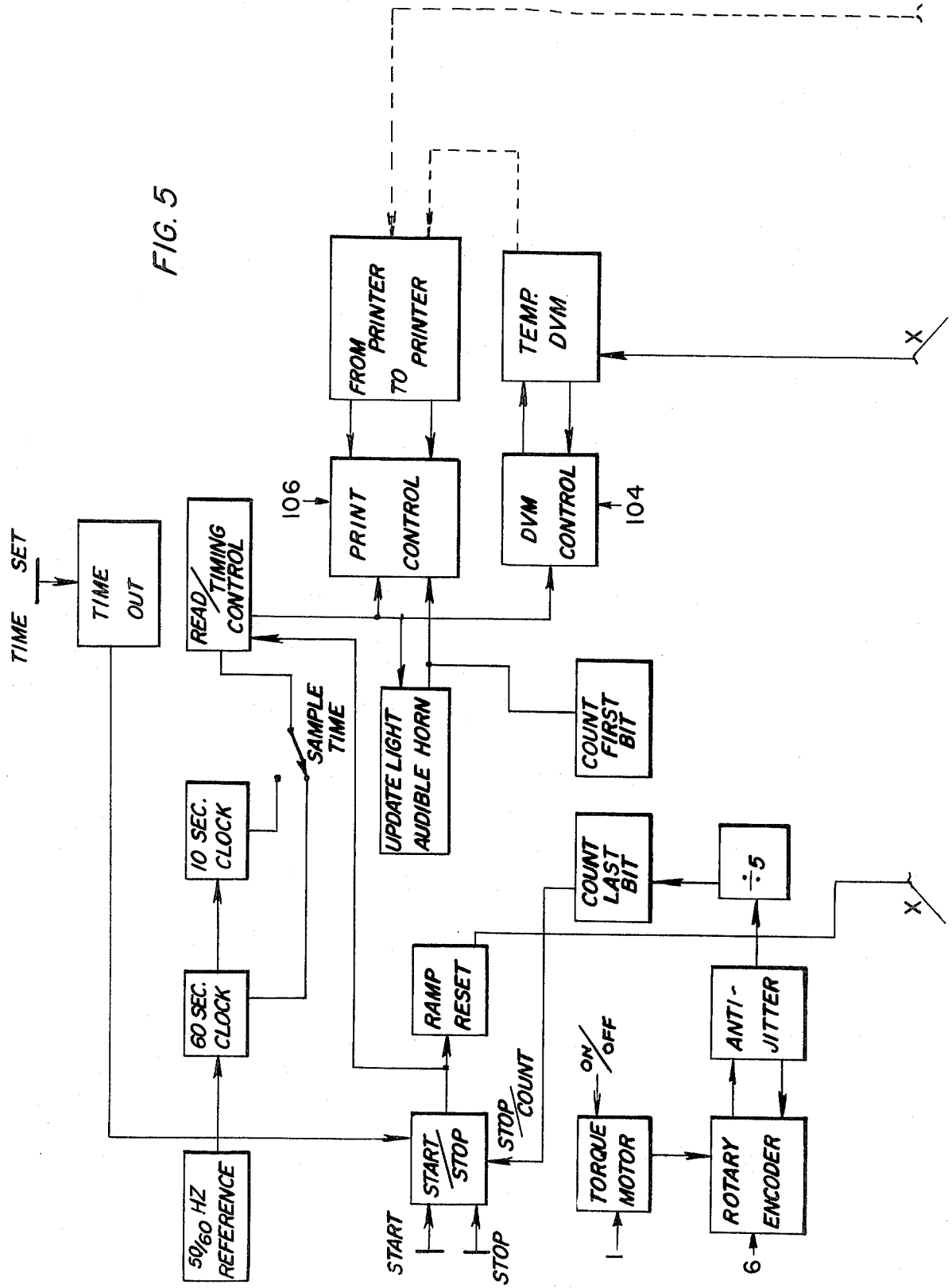

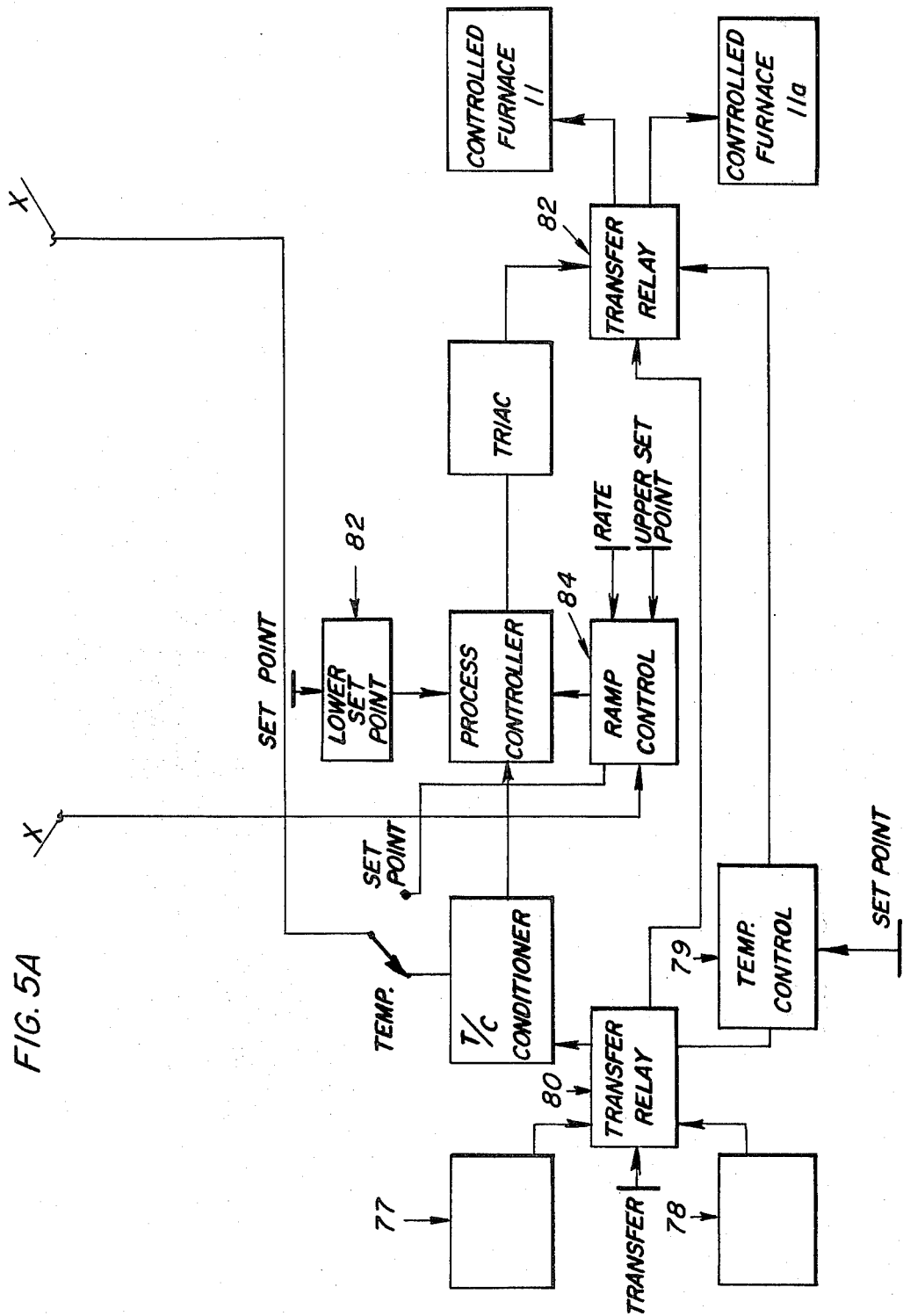

PRE-SET AUTOMATICALLY OPERABLE MEANS FOR MEASURING THE PLASTICITY OF TEST SPECIMENS INCLUDING APPARATUS FOR INDICATING AND RECORDING THE RESULTS THEREOF

The present invention relates to pre-set, automatically operating means for accurately measuring the plastic characteristics of test specimens or samples, and particularly to heated test specimens of coal; the same including automatically operating instrumentalities for indicating and recording certain of the results of the test, as well as informing the operator of the progross being made from time-to-time.

Like many materials, as coking coals are heated they soften and become plastic.

In the selection of coals for carbonization the fluidity as well as the temperature range are essential.

A plastometer measures the intial temperature at which the coal softens, the maximum fluidity, and the final temperature at which the coal solidifies. The range of plasticity is represented by the degrees of temperature between the initial temperature and the final temperature.

The best presently known embodiment of the apparatus of the invention is its association with plastometers which measure the plastic characteristics of coal, and particularly plastometers therefor which are known in the trade as Gieseler Constant Torque Plastometers. In the Gieseler Constant Torque Plastometer, a driving motor is connected through a hysterisis brake to a stirring rod which extends downwardly into the heated specimen or sample undergoing testing. As the sample plasticizes due to the heat from the heated container, a rotary optical encoder, which is associated with the shaft of the driving motor counts electrical pulses as a measure of shaft rotation. Such instruments have for a number of years been used to measure the plastic characteristics of coal; and are specifically described in American Society for Testing Materials Designation D 2639-71 and Designation D 1812-69 (Reapproved 1974), etc.

As the immediate foregoing clearly indicates, Gieseler plastometers have met with some considerable degree of success because of their utility for their intended purpose, including accuracy, etc.

However, and as will become more readily apparent as this description proceeds, Gieseler plastometers have, up to the time of the present invention, been characterized by a mode of operation which involves the heating of a test specimen (coal) to desired temperature, the testing of that particular specimen, the observation of the results thereof, and the re-utilization of the container of the now-tested specimen for a new test specimen. Also, the standard Gieseler plastometers require the fairly close attention of the operator thereof throughout the entire specimen-testing process, which prevents operator from being otherwise employed.

It is among the objects of the present invention to provide an essentially automatically operating pre-set apparatus which will, with little or no attention of the operator fully conduct and fully control a complete Gieseler-type plastometer test, said apparatus including means for furnishing full information with respect to the results of the test and the status being made therein which comprises, among other things, means for signalling or indicating any malfunction in the apparatus, such as the improper heating of the test specimen or the improper stirring of the test specimen.

A further object is the provision of the foregoing objects and advantages while maintaining the highest degree of accuracy and efficiency.

A still further object is the provision of apparatus for accomplishing all of the foregoing which is speedily and easily operated by the technician in charge thereof, durable in service, and yet relatively simple and inexpensive to manufacture and maintain.

The foregoing and other objects and advantages will become more readily apparent as the following description proceeds, the same to be read in conjunction to the appended drawings wherein like reference numberals refer to like parts, and wherein:

FIG. 2 is an enlarged elevational view taken on the line 2—2 of FIG. 1;

FIG. 3 is a perspective of the operating elements of the torque-testing components of the apparatus;

FIGS. 5 and 5A represent in block diagram form various components which may suitably be utilized for operating and controlling the apparatus of FIGS. 1 and 2 in the manner described hereinbefore; the two Figures being divided along the line X for convenience;

DESCRIPTION OF THE PREFERRED EMBODIMENT

Figure 1:
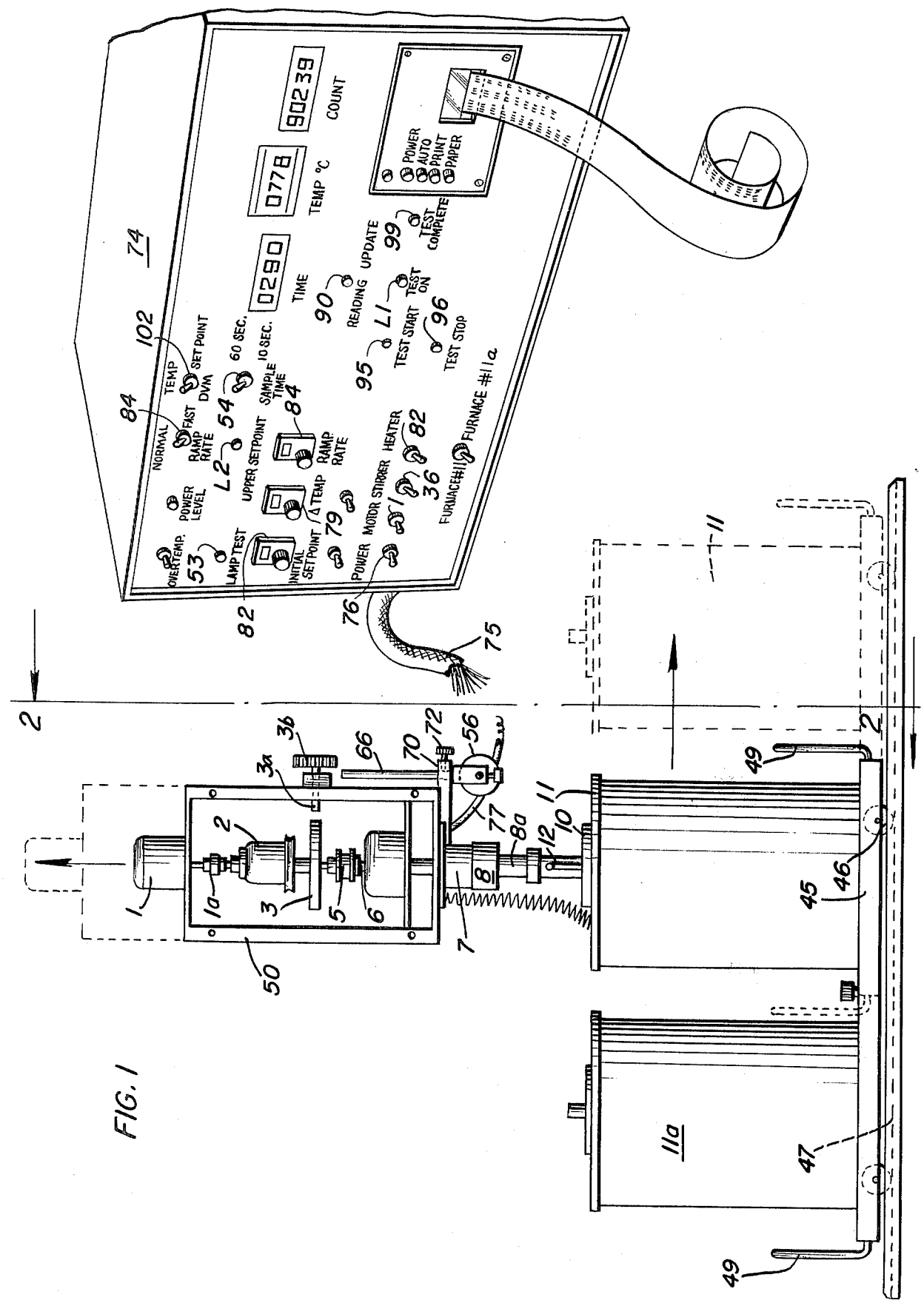
FIG. 1 is an elevational view of the operating elements of the apparatus of the invention together with a perspective of an adjacently disposed control panel or box which contains the control elements and the electrical and electronic components.

In FIG. 1 of the drawings there is represented a plastometer embodying the teachings of the invention which is generally of the Gieseler type, but with certain modifications therein and additions thereto. As in the instance of the typical Gieseler plastometer, the illustrative embodiment comprises a vertically disposed synchronous electric motor 1 with its shaft connected through an electrically-operated clutch or coupling 1a with a hysterisis brake 2 which is immediately therebelow.

The lower end of the shaft of the hysteresis brake 2 is connected to a vertical shaft which carries a brake disc or drum 3 that is contacted, when desired, by a suitable stop member 3a that is moved toward and away therefrom by a screw-and-knurled nut 3b (see FIG. 1) or other suitable instrumentality.

The lower end of the vertical shaft on which the manully operated brake disc or drum 3 is mounted is connected by a flexible coupling 5 with the upper end of a vertically disposed optical shaft encoder 6, the purpose and operation of which will be specifically described hereinafter.

The lower end of the vertical shaft of the optical shaft encoder 6 is suitably connected to a spindle housing 7 comprising a lower knurled connecting nut 8 that connects with the upper end of a shaft housing 8a (FIG. 2) for the stirrer which is to stir the sample to be tested.

To the upper portion of the shaft housing 8a there is secured a cylindrical cover 10 for covering the upper end of the hollow interior of a cylindrical electric furnace 11 containing the specimen to be tested and atop this cover 10 there is disposed a gas vent tube 12 which extends downwardly into said recess, as well as a mounting 14 (FIG. 2) for a vertical shaft 16 carrying a pulley 18, the purpose of which will be described shortly hereinafter.

Referring to FIG. 2, the lower end of the shaft housing 8a communicates with a removable crucible 20 within the hollow interior of the cylindrical electric furnace 11 which contains the specimen to be tested.

Extending downwardly through the spindle housing 7 is a shaft 22, the lower end of which is adapted to be positioned within the crucible 20 and which carries radially extending agitator pins 24 for agitating the specimen during the test.

The aforementioned vertical shaft 16, which is secured to the pulley 18 atop the cover 10, extends downwardly into the hollow interior of the cylindrical electric furnace 11 alongside the crucible 20 and carries a stirring blade 26 which is for the purpose of stirring the molten lead, or lead-tin mixture of equal proportions, which, according to the prior art, surrounds the crucible and maintains the temperature therein at proper levels during the testing of the sample.

Also, extending through the cover 10 is an opening (not shown) for the leads of a thermocouple 28 which is disposed in a recess 29 in the side wall of the hollow interior of the cylindrical electric furnace 11.

According to the present invention at the right hand side of the apparatus of FIG. 2, there is an appropriately supported vertical column 30 which extends to a position in the above described apparatus which is slightly below the lower end of the optical shaft encoder 6; and this vertical column carries a vertically adjustable inwardly extending arm 32 which is connected to and supports the spindle housing 7.

The vertical column 30 also carries a second vertically adjustable inwardly extending arm 34 which supports an electric motor 36, the shaft of which extends vertically and carries a pulley 38 that is connected to the pulley 18 by means of a Jones spring belt 40.

Secured to the shaft housing 8a for the shaft 22 for the stirrer (pins 24) for agitating the testing specimen in the crucible 20 in the electric furnace 11 is a right-angularly extending handle 44 by means of which the operating elements of the Gieseler-type apparatus hereinbefore described may easily and quickly be manually raised and lowered with respect to the cylindrical electric furnace therebelow, thus facilitating the removal of a container with a crucible holding the specimen which has just been tested and the replacement thereof being a container having a crucible with a new specimen which is to be tested.

According to the teachings of the present invention, several of the specimen-containing cylindrical electric furnaces 11 and 11a are disposed on a rectangular manually movable flat carriage 45 which is provided along its edges with a series of rollers 46 that ride in grooves 47 in a base plate 48 which is disposed therebeneath, said movement being facilitated by conveniently disposed handles 49 at one or both ends of the carriage 45.

That portion of the apparatus which includes the hysteresis brake 2, brake drum 3, flexible coupling 5 and rotary encoder 6, is shown in FIGS. 1 and 2 as enclosed by a rectangular housing 50.

The hysteresis brake 2 is capable of slight adjustment, for example from 11.4 to 114-g.in. torque. The torque may be checked in any one of several different methods, one of which, as shown in FIG. 3, comprises a pulley 52 which is secured to the shaft 22 that carries the agitator pins 24 (see FIG. 1) at its lower end. A string or very light flexible cable 54 is attached to the pulley 52 and extends over a second pulley 56 to depend downwardly therefrom for a short distance for attachment to an appropriate weight 58.

As shown in FIG. 3, the second pulley 56 is rotatably mounted on one end of a horizontally extending shaft 62 which is slidably disposed in an aperture extending through a rectangular block 64, a thumb-screw 65 being provided for securing the horizontally extending shaft (62) in longitududinally adjusted position.

The upper portion of the rectangular block 64 is secured to the lower end of a rod 66 which extends upwardly through a vertically extending aperture in a bar 70 which extends horizontally and is secured to the bottom of the housing 50. The vertically extending rod 66 is secured in appropriate vertical position by means of a thumb-screw 72.

With the aforementioned parts of the apparatus in the positions described, and with the fixed-speed motor 1 in operation, the hysteresis brake 2 is adjusted until the weight 58 is held in suspension.

Immediately following the torque adjustment the weight-supporting elements as shown in FIG. 3 are moved into inoperative position, and will not interfere with the operation of the head of the plastometer.

Referring to the right-hand side of FIG. 1 of the drawings, a control panel or box 74 contains the electric control elements and the indicating and recording instrumentalities through which the desired automatic operation of the apparatus of the invention is achieved. As shown, a cable 75 contains wiring for appropriately connecting the various electrical and/or electronic components, as will be described hereinafter, and as are illustrated in FIG. 1 and the block diagrams and circuitry of FIGS. 5 and 5A the drawings.

The front of the control panel 74 contains, for the convenience and information of the technician or operator, the various control elements and indicating and recording instrumentalities referred to together with one or more apertures for the passage therethrough of printed readouts in tape form.

All of the individual components of the aforementioned control elements, indicating and recording instrumentalities are readily available on the open market and as such form no part of the present invention.

THE ALTERNATING CURRENT CIRCUIT

Figure 4:
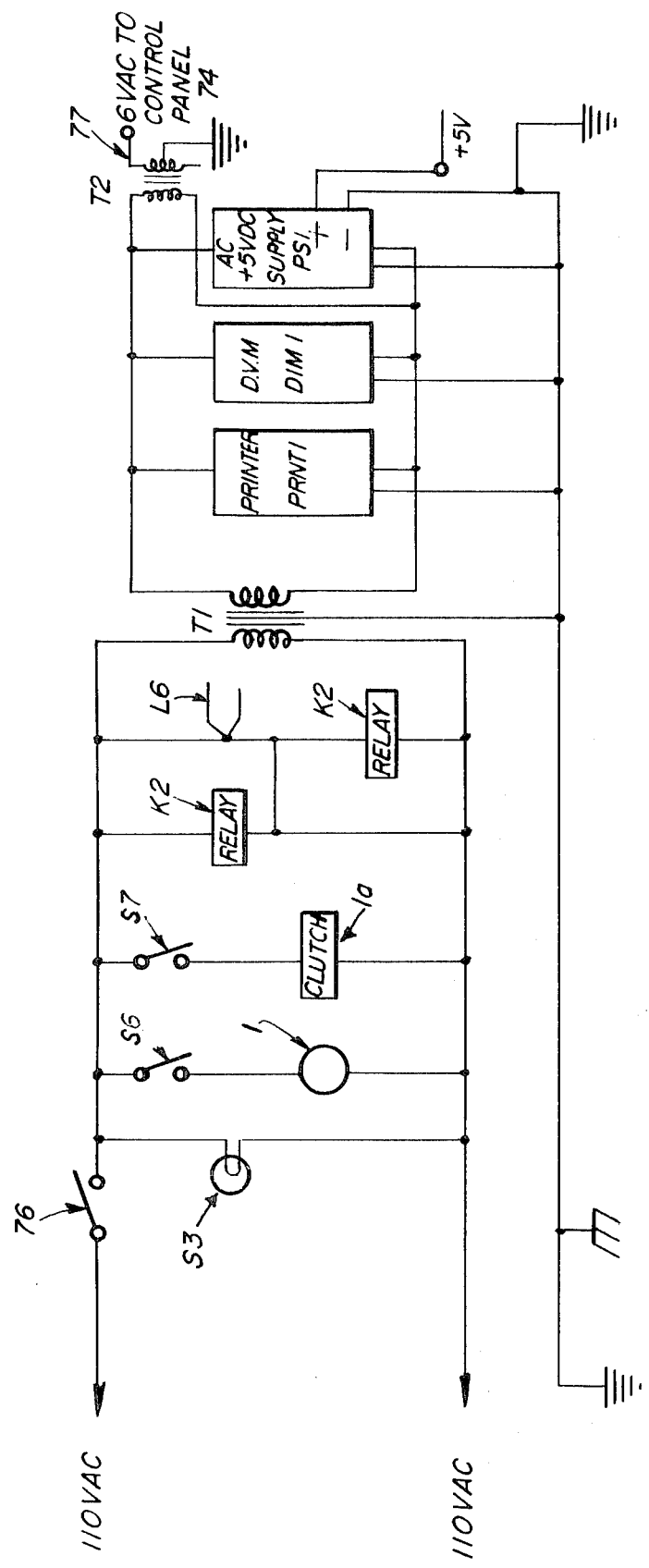
FIG. 4 is a general wiring diagram of the 110 -Volt alternating current portion of an illustrative embodiment of the electrical circuitry of the apparatus.

Referring to the diagram of FIG. 4, the power switch 76 contols all power to the apparatus, and as indicated on the front of the control panel 75 of FIG. 1 individual switches are provided for the constant speed electric motor 1, the electric motor 36 which drives the pulleys 38 and 8 and the Jones Spring Belt 40 and power to facilitate setting-up procedures and trouble-shooting.

As will be further described hereinafter, in the event a dangerous temperature rise should occur, relay K2 FIG. 4 will turn on, with a set of contacts locking this relay on and energizing the overtemperature indicator L6. This relay K2 also removes power from the circuit to the heating means for the test specimen containers.

The apparatus is reset after an overtemperature situation by momentarily removing power through the power switch 76.

Referring to the right-hand portion of FIG. 4, transformer T.1 provides a source of isolated and shielded 110-Volt alternating current for the Printer and the logic assembly labelled DVM. Since these components are susceptible to electrical noise on the alternating current all ground connections to this part of the circuit are run preferably directly back to the incoming power line ground, as shown.

TEMPERATURE CONTOL CIRCUIT

Referring to the left-hand end of the block diagram of FIG. 5A, temperature control modules 77 and 78 are powered directly from the 110-V alternating current line and are connected with the temperature control apparatus 79 through the module 80 which is labelled TRANSFER RELAY 82. Each temperature control module has its own internal isolation transformer. Whereby all signal interconnections can be floating except for a single external ground reference where desired.

The first temperature control module 77 produces a voltage proportional to temperature, one volt direct current per each one hundred degrees Celsius. The temperature, and thus the output of temperature control module 77 is the controlled variable in the system.

The output voltages of the temperature control modules 77 and 78 are arithmetically added. The second temperature control module 78 produces a voltage which is proportional to the setting of the first temperature control module 77, thus establishing a base, or lower limit, for the sum of the two voltages, the lower setpoint module being indicated at 82. The ramp control module 84, produces a voltage ramp at its output, which is added to the level established by the second temperature control module 78. The output of the ramp voltage control module output starts at zero. Thus, the sum voltage starts at the level set by the second temperature control module 78, and ends at a level that is the sum of the output of both temperature contols.

CONTROL LOGIC

Referring to the partial diagram of FIG. 5 the signal 6-Volt alternating current is generated by T2 and is a 60 Hz signal. It is clipped and shaped into a rough square wave, and squared by a Schmitt trigger in the one well known in the art. The resulting square wave is the fundamental time base for the apparatus. The multi-second accuracy of the line frequency will be found to be very good, and the long term accuracy excellent. This signal drives a sequency of counters U2, U3, U4, U5, and so on to derive timing signals of 0.1 second, 1 second, 10 seconds, 1 minute, etc. These counters will only be operative while a test is in progress, since they are held in the over-riding reset mode by Signal L1 TEST ON, as indicated on control panel 75, until an actual test is begun.

Typically, the standard Schmitt trigger circuit embodies gates which form a cross-coupled pair, or latch. A momentary low level on TEST START, indicated at 95 on control panel 75, will make the latch reside so that TEST ON L1 on the control panel is high or true. A momentary low on TEST STOP 96 will flip the latch of the Schmitt trigger circuit so that TEST ON, L1, is high. Other signals may also flip the latch if desired, insuring that the latch of the Schmitt trigger circuit begins with TEST ON, L1, low. After initial turn-on, the POWER UP RESET should remain high. The signal TEST COMPLETE, as indicated at 99 on the control panel 75, also will automatically flip the latch at the end of the test. This signal also locks out the TEST START signal 95 so that a new test cannot be inadvertently started, until after TEST STOP 96 and the signal TEST COMPLETE 99 have occurred.

As earlier indicated, the state of the latch of the standard Schmitt trigger circuit is indicated by L1, TEST ON lamp. Switch 83 for LAMP TEST will energize this TEST ON lamp L1, and all others in the logic system. The latch of the Schmitt trigger circuit also controls a relay which releases the appropriate temperature module so that and temperature ramping may begin. At the end of the ramping period, signal indicating that the ramp is done may be used to energize the lamp L2, UPPER SETPOINT on the control panel.

Switch S4, marked SAMPLE TIME, on the control panel 75 may be used to select either the 1/60 Hz or the 1/10 Hz signal. Whichever signal is selected becomes the signal 90 READING UPDATE on the control panel, which occurs either once per ten seconds or once per minute. The rising edge of this signal triggers one-shot U10, which generates a 1-second pulse, and energizes the READING UPDATE lamp 90. This same pulse may also activate a Sonalert or other alarm (not shown) provided the signal the first count is true. The signal DONE SIGNAL will also activate a Sonalert or other alarm, as will the LAMP TEST signal S3.

READING UPDATE 90, on its rising edge, also triggers various one-shots whose signals control the totalizing counter and printer at the end of each reading interval.

Transformer T1 (FIG. 4) produces the count signal to strobescopes which are identical and are required to meet the load requirements on their outputs. This signal transfers the totalized count of the rotary encoder (optical shaft encoder) 6 contained in the decade counters into the equivalent number of latch storage devices. This produces a buffered output for display and printer input.

The signal becomes true when the five decade (for example) counter registers its first count from the rotary encoder 6. This signal enables the Sonalert or other alarm drive circuit and the printer command circuit. It becomes true when the first signal is set by the signal COUNT FIRST BIT (FIG. 5), which comes from the $Q_0$ output of the first decade counter. When this FIRST BIT is toggled true, the signal for the FIRST COUNT BIT becomes true and stays true until re-set by the signal TEST ON L1 going false.

Before a test is initiated, the standard components of the apparatus are set by the signal TEST ON L1 being false. From the foregoing description and the disclosures of FIGS. 4, 5 and 5A, it is believed that the operation of the individual standard components, and others with which they are connected, will be understood to an extent which supports the objectives of the invention and the appended claims.

We claim:

1. A pre-set apparatus for automatically heating and measuring the plasticity of heated specimens of coal and other material and automatically indicating and/or recording the plasticity thereof, said apparatus comprising, in combination,
   (a) a plurality of adjacently disposed containers for holding the specimens to be tested;
   (b) means for heating the specimens in said containers to heating temperature;
   (c) said adjacently disposed heated containers being adapted for successive movement into specimen-testing position;
   (d) a vertically extending support including a lateral extension;

(e) a substantially vertically disposed rotatable stirring rod carried by said support and adapted to extend downwardly into a heated specimen which is in specimen-testing position;

(f) a drive motor carried by said support and adapted to rotate said stirring rod;

(g) a brake connected between said drive motor and said rotatable stirring rod for controlling the amount of torque applied by said drive motor to said stirring rod;

(h) means for measuring movement of the rotatable stirring rod as the test specimen plasticizes;

(i) said last-named means including a rotary optical encoder operatively engaged for rotation with said rotatable stirring rod;

(j) said rotary optical encoder including a rotary member possessing calibrated light-penetrable portions;

(k) a light source for applying light to one side of the calibrated light-penetrable portions of the rotary member of said optical encoder;

(l) said rotary optical encoder including optical sensing means positioned to receive light rays passing through the aforementioned light-penetrable portions of the aforementioned rotary member;

(m) a counter connected to the optical sensing means for recording movement of said stirring rod within a given time reference;

(n) a crucible in each of said adjacently disposed containers for holding the specimens to be tested;

(o) a test specimen within each of said crucibles (p) means surrounding each of said crucibles for heating the test specimen therewithin;

and (q) translatory movable means for successively moving each of said containers into position below said stirring rod.

2. The apparatus of claim 1, together with means for heating the crucible as comprising a molten substance, and a rotatable stirrer for said molten substance, the means for rotating said last-named stirrer including a vertically extending shaft and driving means therefor, both of which are carried by said aforementioned horizontally extending support.

3. The apparatus of claim 1, together with means for signalling or indicating any malfunction therein, including the improper heating of the test specimen and the improper stirring of the test specimen.

4. The apparatus of claim 1, together with means for indicating and/or recording all of the results of the test.

5. The apparatus of claim 1, together with means for indicating and/or recording the temperature of the heated test specimen and the length of time consumed by the testing of the test specimen so heated.

6. The apparatus of claim 1, together with means for indicating the condition that a specimen is in the process of being tested.

7. The apparatus of claim 1, together with means for indicating the completion of the test of a specimen.

8. The apparatus of claim 4, which includes a logic control assembly.

9. The apparatus of claim 4, which includes a logic control assembly and a printer.

10. The apparatus of claim 4, which includes a logic control assembly and a counter.

* * * * *